United States Patent
Van Zon et al.

(10) Patent No.: US 9,488,647 B2
(45) Date of Patent: Nov. 8, 2016

(54) DETECTION OF SURFACE-BOUND MAGNETIC PARTICLES

(71) Applicant: KONINKLIJKE PHILIPS N.V., Eindhoven (NL)

(72) Inventors: Joannes Baptist Adrianus Dionisius Van Zon, Waalre (NL); Ron Martinus Laurentius Van Lieshout, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 26 days.

(21) Appl. No.: 14/355,444

(22) PCT Filed: Oct. 31, 2012

(86) PCT No.: PCT/IB2012/056044
§ 371 (c)(1),
(2) Date: Apr. 30, 2014

(87) PCT Pub. No.: WO2013/064990
PCT Pub. Date: May 10, 2013

(65) Prior Publication Data
US 2014/0287533 A1 Sep. 25, 2014

Related U.S. Application Data

(60) Provisional application No. 61/555,147, filed on Nov. 3, 2011.

(51) Int. Cl.
*G01N 21/74* (2006.01)
*G01N 33/543* (2006.01)
*G01N 21/552* (2014.01)
*G01N 27/74* (2006.01)

(52) U.S. Cl.
CPC .......... *G01N 33/543* (2013.01); *G01N 21/552* (2013.01); *G01N 27/745* (2013.01)

(58) Field of Classification Search
None
See application file for complete search history.

(56) References Cited

U.S. PATENT DOCUMENTS

| | | | |
|---|---|---|---|
| 5,491,068 A | 2/1996 | Benjamin et al. | |
| 2005/0048599 A1 | 3/2005 | Goldberg et al. | |
| 2009/0227044 A1 | 9/2009 | Dosev et al. | |
| 2009/0251136 A1* | 10/2009 | Prins ............ | B82Y 25/00 324/228 |
| 2010/0109653 A1* | 5/2010 | Nieuwenhuis ....... | B82Y 25/00 324/204 |

FOREIGN PATENT DOCUMENTS

| | | | |
|---|---|---|---|
| WO | 2006079998 A1 | | 8/2006 |
| WO | 2008155716 A1 | | 12/2008 |
| WO | WO2009/112984 | * | 9/2009 |
| WO | 2009125356 A1 | | 10/2009 |
| WO | 2010035174 A1 | | 4/2010 |
| WO | 2010084383 A1 | | 7/2010 |

* cited by examiner

*Primary Examiner* — Rebecca Martinez

(57) ABSTRACT

A method detects magnetic particles (1) bound to a binding surface (111) of a sample chamber (112). The detection is made during and/or immediately after the action of an attractive magnetic field. The attractive magnetic field (B) is preceded by a repulsive magnetic field (B) which removes unbound magnetic particles away from the binding surface (111). Due to the attractive magnetic field (B), bound magnetic particles (1) come closer to the binding surface (111), which increases the signal of surface specific detection techniques like frustrated total internal reflection. The signal can be achieved by an attractive magnetic field that is parallel to the binding surface (111) thus inducing the generation of chains between unbound and bound magnetic particles.

19 Claims, 2 Drawing Sheets

DETECTION OF SURFACE-BOUND MAGNETIC PARTICLES

CROSS-REFERENCE TO PRIOR APPLICATIONS

This application is the U.S. National Phase application under 35 U.S.C. §371 of International Application No. PCT/IB2012/056044, filed on Oct. 31, 2012, which claims the benefit of U.S. Provisional Patent Application No. 61/555,147, filed on Nov. 3, 2011. These applications are hereby incorporated by reference herein.

FIELD OF THE INVENTION

The invention relates to a method and a sensor device for the detection of magnetic particles that are bound to the binding surface of a sample chamber.

BACKGROUND OF THE INVENTION

The WO 2008/155716 discloses an optical biosensor in which frustrated total internal reflection (FTIR) of a light beam is detected and evaluated with respect to the amount of magnetic particles at a binding surface. Magnetic fields are used to attract the magnetic particles to said surface for an accelerated binding and to wash unbound magnetic particles away before a detection is made.

SUMMARY OF THE INVENTION

It was an object of the present invention to provide means for a quantitative detection of surface-bound magnetic particles that have an improved sensitivity.

The method according to the present invention serves for the detection of magnetic particles that are bound to the binding surface of a sample chamber.

In this context, the term "magnetic particles" shall comprise both permanently magnetic particles as well as magnetizable particles, for example superparamagnetic beads. The size of the magnetic particles typically ranges between 3 nm and 50 µm. Moreover, the magnetic particles may comprise bound target components one is actually interested in. The "sample chamber" is typically an open cavity, a closed cavity, or a cavity connected to other cavities by fluid connection channels. The "binding surface" of the sample chamber is just one dedicated interior surface of this chamber that can be contacted by the magnetic particles or other entities and at which their detection can take place by an appropriate method. As its name indicates, the binding surface will usually be provided with binding sites at which magnetic particles can specifically bind.

The method comprises the following steps:

a) Generating a magnetic field that attracts magnetic particles to the binding surface. Due to this effect, said magnetic field will in the following be called "attractive magnetic field". This attractive magnetic field shall prevail at the binding surface and in at least a part of the sample chamber. To generate its attractive effect on the magnetic particles, the magnetic field will typically have a nonzero gradient.

b) Detecting magnetic particles at the binding surface during and/or immediately after the aforementioned step, i.e. the generation of an attractive magnetic field. In this context, the term "during" shall generally comprise a continuous detection throughout the whole period the attractive magnetic field is present or a detection at one or several distinct time points/intervals within this period. The term "immediately" shall denote the period when the attractive magnetic field has already been switched off but the magnetic particles have not yet moved significant (i.e. detectable) distances. Hence this term is related to the relaxation time of the effect of the magnetic field and the extent of Brownian motion of the particles (which is typically lower near a surface than in the bulk due to an increased viscosity near the surface).

It should be noted that the aforementioned steps are usually preceded by preparations inherent to the method, for example by the provision of a sample with magnetic particles in the sample chamber and a binding period during which the magnetic particles are allowed (with or without active assistance) to bind to the binding surface.

A sensor device according to the present invention serves for the detection of magnetic particles that are bound to the binding surface of a sample chamber and comprises the following components:

a) A magnetic field generator for generating an attractive magnetic field that attracts magnetic particles to the binding surface. The magnetic field generator may for example be realized by a permanent magnet or an electromagnet.

b) A detection unit for detecting magnetic particles at the binding surface.

c) A control unit for controlling the detection unit and the magnetic field generator such that a detection is made while magnetic particles are attracted to the binding surface and/or immediately thereafter. The control unit may be realized by dedicated electronic hardware, digital data processing hardware with associated software, or a mixture of both.

The method and the sensor device are different realizations of the same inventive concept, i.e. the detection of magnetic particles under the effect of an attractive magnetic field. Explanations and definitions provided for one of these realizations are therefore valid for the other realization, too.

It has turned out that the accuracy and the sensitivity of the detection of magnetic particles can be increased by the proposed concept. This comes as a surprise as it is usually considered as being inevitable to do measurements during the action of a repulsive magnetic force that washes unbound magnetic particles away from the surface (cf. WO 2008/155716).

In the following, various preferred embodiments of the invention will be described that relate both to the method and the sensor device defined above.

An evaluation unit may preferably be provided for evaluating the detection results (signals) that are produced during the detection procedure, wherein said evaluation is done with respect to the amount of magnetic particles bound at the binding surface. The evaluation unit may be a component of its own of be integrated with the control unit.

The magnetic particles at the binding surface may preferably be detected at a time point lying between about 0.01 s and about 1 s after the start of the attractive magnetic field, preferably at about 100 ms after the start. Such a detection very shortly after the beginning of magnetic attraction has the advantage that predominantly the bound magnetic particles rather than unbound ones show a detectable reaction to the attractive magnetic field, because they are already close to the binding surface.

According to another embodiment of the invention, a further magnetic field is generated that pulls magnetic particles away from the binding surface, wherein this magnetic field is generated prior to the attractive magnetic field. With reference to its effect, the further magnetic field will in the following be called "repulsive magnetic field". The repulsive magnetic field has the advantage that it removes unbound magnetic particles from the binding surface. During the following action of the attractive magnetic field, it are therefore first only the bound magnetic particles that come closer to the binding surface (in the range allowed by their bindings), thus generating a detectable effect. The unbound magnetic particles, on the contrary, must first travel the distance they have previously been washed away by the repulsive magnetic field before they reach the binding surface.

In the aforementioned embodiment, the duration and/or the strength and/or the gradient of the repulsive magnetic field is preferably larger than the duration and/or the strength and/or the gradient, respectively, of the attractive magnetic field. This means that, on average, unbound magnetic particles will be moved farther away from the binding surface by the repulsive magnetic field than they are attracted towards the binding surface by the attractive magnetic field. Accordingly, the binding surface will still be free of unbound magnetic particles while the detection is made.

The above described sequence of first a repulsive magnetic field and then an attractive magnetic field is preferably repeated two or more times (with or without intermediate intervals). Thus a plurality of detection results can be collected during the phases of magnetic attraction. This increases the statistical significance and allows to exclude events, which can experimentally be observed, during which the attractive magnetic field shows no particular effect on a bound magnetic particle.

In general, any method may be applied for the detection of magnetic particles at the binding surface. Preferably, surface specific techniques are used that are only sensitive in a region close to the binding surface. One preferred technique of this kind makes use of evanescent light waves for the detection of magnetic particles at the binding surface. Evanescent waves have the advantage that they affect only a small region adjacent to the binding surface and are thus suited for selectively sensing monolayers of (magnetic) particles.

The aforementioned evanescent waves may optionally be generated by total internal reflection of a light beam at the binding surface. Detection with a light beam that is totally internally reflected at the interface between a transparent material and an adjacent sample fluid is a technique known as frustrated total internal reflection (FTIR).

According to another embodiment of the invention, an image sensor is provided for the detection of an output light beam coming from the binding surface. This output light beam may for example be generated in the above mentioned way by (frustrated) total internal reflection of an input light beam. Detection of an output light beam with an image sensor has the advantage that the binding surface can simultaneously be observed and evaluated at many positions (represented by pixels or groups of pixels of the image sensor).

In the aforementioned embodiment, the shutter time and/or the frame rate of the image sensor is preferably synchronized with the generated (attractive and/or repulsive) magnetic field. Thus it can be guaranteed that an image of the binding surface is generated at the right point in time, i.e. typically shortly after the start of the attractive magnetic field.

The attractive magnetic field is preferably parallel to the binding surface or has at least a component parallel to the binding surface. It should be noted in this context that the direction of the magnetic field (i.e. of the magnetic field lines) is different from the direction of the field gradient which determines the magnetic force generated on a magnetic particle; in general, the gradient may have any direction oblique to the field lines. In a magnetic field parallel to the binding surface chains between bound and unbound magnetic particles are formed that are parallel to the surface. In this way the signal associated to the bound magnetic particles will be enhanced.

The invention further relates to the use of the sensor device described above for molecular diagnostics, biological sample analysis, chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiments described hereinafter.

In the drawings.

Like reference numbers refer in the Figures to identical or similar components.

DETAILED DESCRIPTION OF EMBODIMENTS

Instruments for the detection of Nuclear Acids (DNA, RNA), metabolites (molecular diagnostics), and proteins (immuno-assays), which may be markers for all kind of diseases in the human body, have become an important component in healthcare. A typical immuno-as say technique uses small superparamagnetic particles (beads) as labels to detect the presence of target molecules in a solution. For example the target molecule can be the troponin-I protein (cTnI) which is used as a marker for the detection of myocardial infarction. These labels are coated with antibodies which specifically catch target molecules. After binding to a surface which is also coated with functional antibodies, the magnetic labels are detected by means of e.g. an optical detection technique. Frustrated Total Internal Reflection (FTIR) may for instance be used to measure the bead density on the surface. In this technique a light beam from an illumination source such as a laser or LED hits a surface under a critical angle at which total reflection of the light beam occurs.

Figure 1:
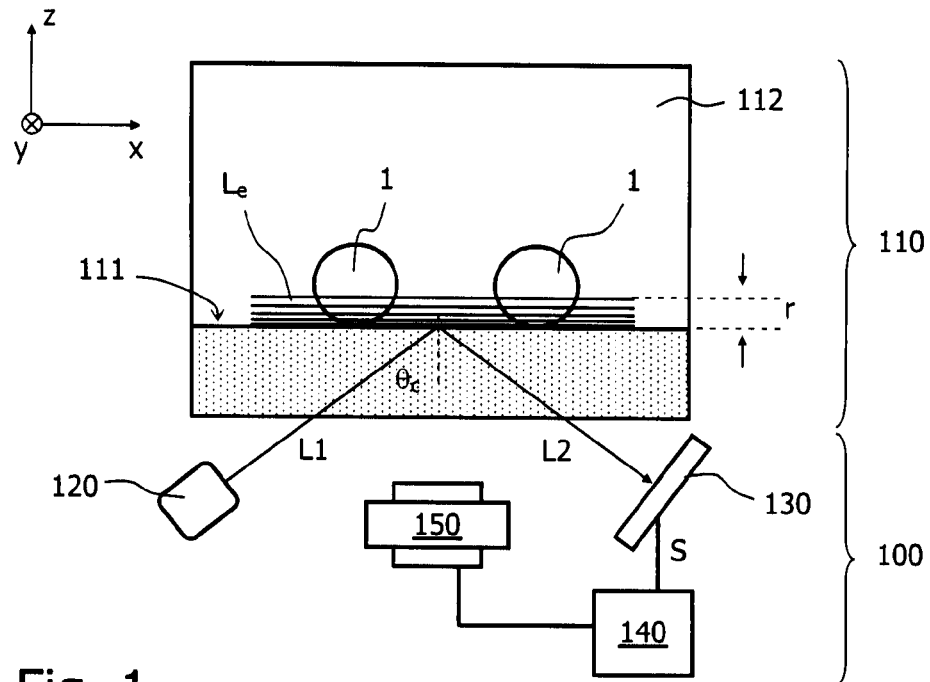
FIG. 1 illustrates the detection of bound magnetic particles by frustrated total internal reflection (FTIR) in a schematic side view of a sensor device according to the present invention.

FIG. 1 schematically shows a side view of an exemplary sensor device 100 for FTIR detection of magnetic particles. The sensor device 100 is designed to make optical measurements in a disposable cartridge 110 that may for example be made from glass or transparent plastic like poly-styrene. The cartridge comprises a sample chamber 112 in which a sample fluid with target components to be detected can be provided. The sample further comprises magnetic particles 1, for example superparamagnetic beads 1, wherein these particles 1 are usually bound as labels to the aforementioned target components (for simplicity only the magnetic particles 1 are shown in the Figure).

The cartridge 110 has a transparent bottom with a binding surface 111 that (partially) borders the sample chamber 112. A plurality of "detection spots" are typically disposed on the binding surface 111. They comprise binding sites, e.g. antibodies, which can specifically bind the target components (cf. FIG. 2).

The sensor device 100 comprises a light source 120 for emitting an input light beam L1 such that it arrives at the binding surface 111 at an angle $\theta_c$ larger than the critical angle of total internal reflection (TIR) and is therefore totally internally reflected as an output light beam L2. The output light beam L2 is detected by a light detector, e. g. by the light-sensitive pixels of a camera 130. The light detector 130 thus generates as detection signal S an image of the binding surface, which is further processed in an evaluation and control unit 140.

The sensor device 100 further comprises a magnetic field generator, for example realized by electromagnets 150 with a coil and a core disposed at the bottom and/or at the top (not shown) of the cartridge 110, for controllably generating a magnetic field in the sample chamber 112. With the help of this magnetic field, the magnetic particles 1 can be manipulated, i.e. be magnetized and particularly be moved (if magnetic fields with gradients are used). Thus it is for example possible to attract magnetic particles 1 to the binding surface 111 in order to accelerate the binding of the associated target component to said surface.

At the binding surface 111 an exponentially dampening evanescent wave Le is created. When no magnetic beads are present in the evanescent wave near the surface, no absorption of light takes place and the reflected light beam L2 contains 100% of its original intensity. However when particles are present on the surface, absorption and/or scattering takes place and the intensity of the reflected beam decreases. The intensity $I_{refl}$ of the reflected light beam L2 is therefore a measure for the bead density on the surface. This can be expressed by the following formula:

$$I_{refl} = I_{in} - \beta \cdot \tilde{n} \quad (1)$$

where $I_{in}$ is the incoming intensity of the input light beam L1, $I_{refl}$ the reflected intensity, $\tilde{n}$ the bead density on the surface, and $\beta$ a parameter which determines the signal per bead (the absorption and/or scattering per bead).

When no beads are present on the binding surface, the reflected light has 100% of its original intensity. Small variations in the original intensity as well as tiny deformations of the cartridge material due to temperature gradients in the system cause variations in the reflected light beam intensity (system drift). This limits the performance of the instrument and determines the lowest bead density which can still be measured on the surface. Assuming that the variation in intensity of the reflected beam due to drift is $\Delta I$, the lowest measurable bead density $\tilde{n}_{min}$ is equal to:

$$\Delta I = \beta \cdot \tilde{n}_{min} \rightarrow \tilde{n}_{min} = \frac{\Delta I}{\beta} \quad (2)$$

In many applications, especially the detection of the cardiac marker troponin-I, very low concentrations need to be measured. One way of improving the performance of a sensor device is to increase the signal per bead value $\beta$. As can be seen from Equation 2, increasing the signal per bead $\beta$ will lead to a lower value of the minimal detectable bead density on the surface and thus to lower detectable concentration of troponin-I. In the following, a method will be described with which the signal per bead value $\beta$ can be enhanced.

As illustrated in FIG. 1, an exponentially decaying evanescent wave Le is created near the surface 111 where a light beam is totally internally reflected. The intensity of this evanescent wave is the strongest at the surface and drops exponentially with increasing distance to the surface. A bead 1 which is present in this evanescent wave frustrates the incoming light beam because it absorbs and/or scatters light. The amount of light which is absorbed and/or scattered by the bead is dependent on its position in the evanescent field. A bead which is very close to the surface (and thus present in a strong evanescent field) will absorb and/or scatter more light than a bead which is further away from the surface (and thus present in a weaker evanescent field). The signal per bead value $\beta$ is therefore larger close to the surface than further away from the surface.

The penetration depth of the evanescent field in the shown sensor device 100 may for example be about r=100 nm (being dependent on the wavelength and the exact angle of incidence). This means that at 100 nm the intensity of the evanescent field has dropped to 1/e times the intensity at the surface. In order to determine where the bead is in the evanescent field, the following model is used, which is illustrated in FIG. 2:

In order to catch target molecules T from a sample, the bead 1 is functionalized with a layer of antibodies A which are specific to the target molecule T to be caught, e.g. 560 antibodies which are specific to the troponin-I protein. The size of these antibodies is about 15 nm. In the same way the surface 111 is coated with antibodies L which are specific to another epitope of the target molecule T, for example with 19C7 antibodies. The size of these antibodies is also approximately 15 nm. When a target molecule T has been caught by the antibodies A on the magnetic label particle 1 and the label has finally been bound to the surface 111, the target molecule T is sandwiched between two different antibodies. Since the size of the troponin-I molecules is about 4 nm, the magnetic particle 1 can be a distance $d_0$=(15+4+15) nm=34 nm away from the surface. This is sketched in the left hand part of FIG. 2. Of course this value will be distributed because the orientation of the antibodies is distributed. Moreover there may be more than one monolayer of antibodies present on the surface.

Figure 2:
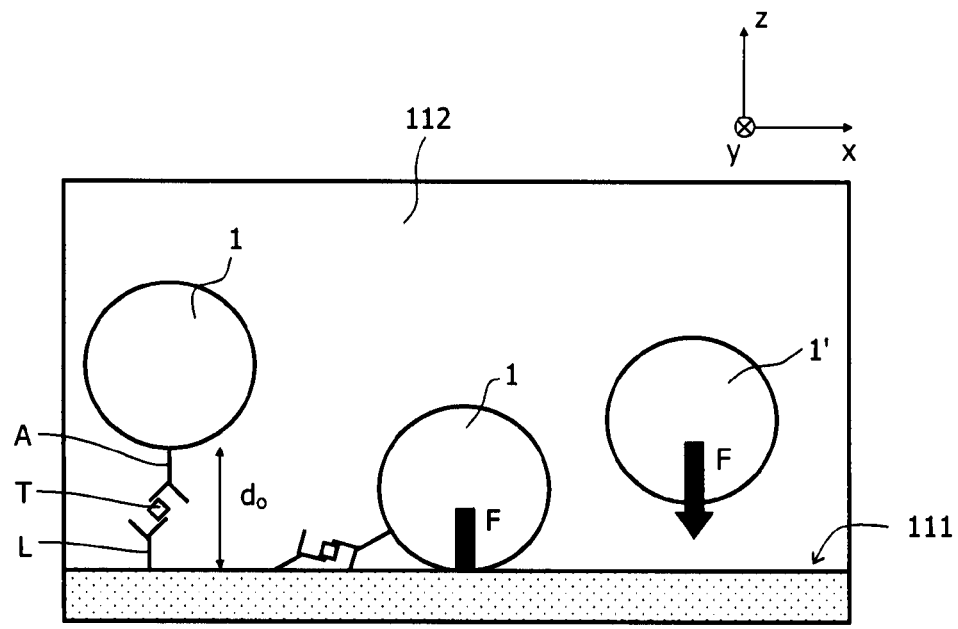
FIG. 2 is an illustration of the effect of an attractive magnetic field on bound and unbound magnetic particles.

The middle part of FIG. 2 shows the situation when a vertical force F directed towards the surface 111 is applied to a bound magnetic bead 1, wherein said force may particularly be generated by a magnetic field gradient. As an effect of the force F, the distance between the bead 1 and the binding surface 111 will be reduced. Because the bead 1 is now closer to the surface, it is in a more intense region of the evanescent field and thus will absorb and/or scatter more light: the signal per bead has been enhanced by the vertical force. In the sensor device 100 of FIG. 1, it is possible to apply such a vertical force F on the bead 1 by generating an attractive magnetic field with the bottom (horseshoe-) electromagnet 150.

As shown in the right hand part of FIG. 2, there are a lot of free floating magnetic labels 1' in the sample, which will also be attracted by the vertical force F and driven towards the binding surface 111. Free floating, unbound labels 1' which are present in the evanescent field near the surface will also absorb and/or scatter light and therefore contribute to the change of the intensity of the reflected light beam.

This will create a false signal, which is a drawback of applying a continuous vertical force to enhance the signal per bead.

A solution to this problem is to apply the vertical force F only for a very short time. The bound magnetic labels 1 are already very close to the surface (<35 nm) and therefore it will only take a very short time to move them closer to the surface. However free floating labels 1' are typically further away from the surface and it will therefore require more time to bring them into contact with the binding surface 111. This difference in time between bound and unbound labels can be exploited by applying only a very short vertical force. A typical time would be less than 0.1 second.

Because of the very short time that the vertical force is present, the enhanced signal per bead is also only available for a very short time. By repetitively using a vertical attractive force (attractive magnetic field) directed towards the surface followed by a vertical repulsive force (repulsive magnetic field) to move the free floating beads away from the surface again, the total time that the enhanced signal per bead is present can be enlarged to increase the statistics of the signal.

In a typical realization of the sensor device 100 of FIG. 1, images from the binding surface are taken by a CCD or CMOS camera 130 using a certain frame rate, e.g. 5 frames per second (FPS). In order to implement the above described approach, it is essential that the shutter time of the camera is short and that the frame rate is synchronized with the driving electronics for the electromagnets 150. This synchronization can be controlled by the evaluation and control unit 140 shown in FIG. 1. It assures that the image is taken at the right moment that the enhanced signal is present. The short shutter time will fully exploit the enhanced signal.

Figure 3:
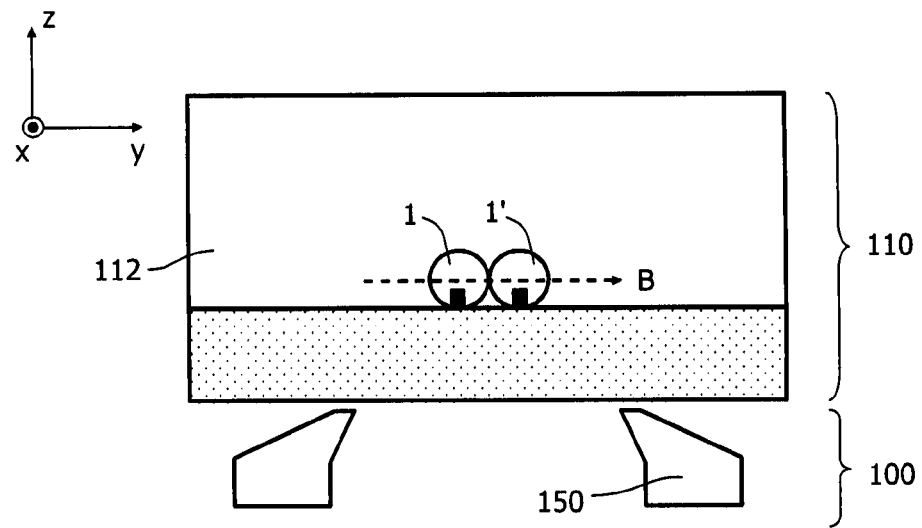
FIG. 3 is a schematic side view of the sensor device according to the present invention illustrating the signal enhancement by a magnetic field parallel to the binding surface.

FIG. 3 shows the sensor device 100 of FIG. 1 in a 90° rotated side view, showing in more detail the bottom horseshoe electromagnet 150. As already mentioned, the vertical force F towards the binding surface 111 may be generated by this electromagnet 150. The magnetic field B produced by this type of magnet is however horizontal (in contrast to the gradient of this field, which is vertical). The horizontal field B will determine the direction of the magnetic clusters (i.e. chains of beads which are magnetically attached to each other due to the presence of the magnetic field). When a vertical force is applied, free floating beads 1' which are very close to the bound beads 1 will be attracted by the bound beads 1 and form small horizontal multiple-particle clusters (e.g. "doublets" of two particles as shown in the Figure). This will lead to another enhancement of the signal which is proportional to the number of bound beads.

The described method has been tested in a setup using an evanescent field. Furthermore, the setup was equipped with a high resolution objective lens which enabled to image individual (500 nm) magnetic beads and therefore measure the real enhancement of the signal per bead. Finally this setup used a perfect synchronization between the driving electronics of the electromagnets and the triggering of the camera. The vertical field directed towards the binding surface was generated by a horseshoe magnet and was switched on during 0.1 s, followed by a period where the vertical field is directed away from the binding surface. In the latter case the magnetic field is generated by a washing magnet above the sample chamber. This sequence of attraction and washing has been repeated several times. From a number of beads which were bound to the binding surface the intensity signal I has been recorded as a function of time t. Because this setup does not use the intensity of the reflected beam but directly the scattered light of the beads, the signal is inverse to the signal of the FTIR setup. A bead which is closer to the surface will scatter more light in the evanescent field and therefore appear brighter in the recorded image.

Figure 4:
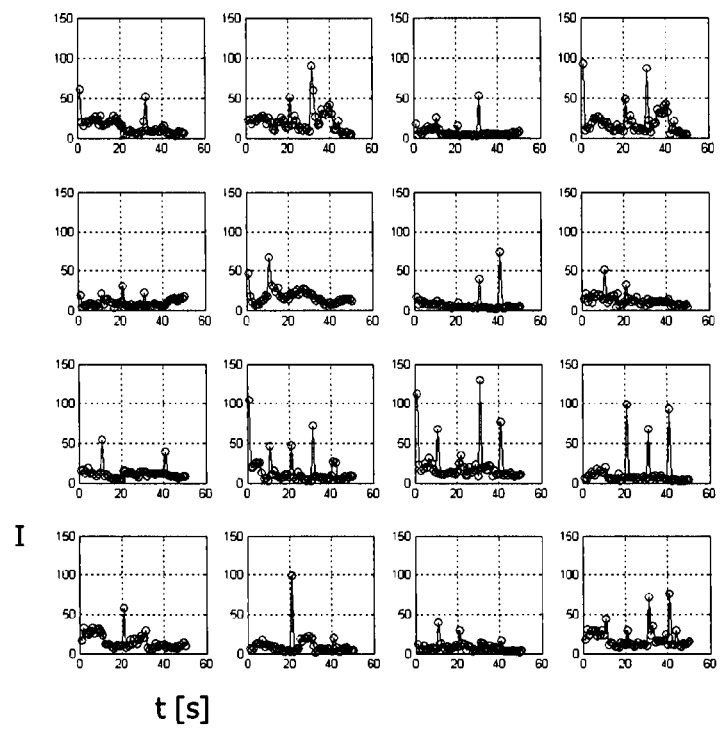
FIG. 4 shows measurement results for bound magnetic beads during an alternation of repulsive and attractive magnetic fields.

FIG. 4 shows for sixteen different beads their recorded intensity signal I during the sequence of attraction and washing. Pulsed signals are observed in which the sudden increase in intensity coincides with the moment where the vertical force towards the surface is switched on. When the washing magnet is switched on to remove the free floating beads again, the intensity drops to the lower level. Although the increase in signal is frequently observed, it does not seem to occur every time. Hence it is favorable to repeat the attraction and washing sequence a number of times.

In summary, the present invention discloses how an enhancement of the signal per bead by using a vertical attraction force can be achieved. When the vertical force is generated by an electromagnet which gives a substantially horizontal magnetic field, small horizontal clusters (e.g. doublets) are formed around the bound beads which will lead to a further enhancement of the signal proportional to the number of bound beads. Other important features of the invention, which can be realized alone or in any combination, are:

The vertical force directed towards the surface is applied only for a limited time to prevent free floating beads from the solution to reach the surface and thereby creates a false signal.

A synchronization between the driving electronics of the electromagnet(s) and the signal taking mechanism (e.g. a camera or photodetector) to fully exploit the enhancement in signal.

A shutter time of the camera or photodetector which is equal to the time that the vertical force directed towards the surface is applied.

An attraction time which is in the order of 0.1 s.

The vertical force directed towards the surface is followed by a vertical force directed away from the surface to move the free floating beads away from the surface. This procedure of moving towards the surface (attraction) and moving away from the surface (washing) is used in a repetitive way to increase the statistics of the enhanced signal.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for the detection of magnetic particles in a sample chamber, comprising:
   a) generating a sequence including a repulsive magnetic field and an attractive magnetic field, wherein
      a1) the attractive magnetic field is configured with a component parallel to a binding surface of the sample chamber to attract magnetic particles to the binding surface;

a2) the repulsive magnetic field is configured to pull magnetic particles away from the binding surface;
a3) a duration and/or a gradient of the repulsive magnetic field is larger than that of the attractive magnetic field;
b) detecting magnetic particles at the binding surface at a time of between about 0.01 s and about 1 s after the start of the attractive magnetic field.

2. A method for the detection of magnetic particles that are bound to a binding surface of a sample chamber, said method comprising:
a) generating an attractive magnetic field that attracts magnetic particles to the binding surface;
b) detecting magnetic particles at the binding surface, wherein said magnetic particles at the binding surface are detected between about 0.01 s and about 1 s after the start of the attractive magnetic field.

3. The method according to claim 2, wherein a repulsive magnetic field is generated that repels magnetic particles away from the binding surface prior to the generation of the attractive magnetic field.

4. The method according to claim 3, wherein a duration, a strength and/or a gradient of the repulsive magnetic field is larger than that of the attractive magnetic field.

5. The method according to claim 3, wherein the sequence of the repulsive magnetic field and the attractive magnetic field is at least twice repeated with the magnetic particles being detected only during the last attractive magnetic field.

6. The method according to claim 2, wherein the magnetic particles at the binding surface are detected using evanescent waves.

7. The method according to claim 6, wherein the evanescent waves are generated by total internal reflection of a light beam at the binding surface.

8. The method according to claim 7, wherein an output light beam coming from the binding surface is detected with an image sensor with a shutter time and/or the frame synchronized with the generated magnetic fields.

9. The method according to claim 2, wherein the attractive magnetic field has a component parallel to the binding surface.

10. The method according to claim 1, wherein the attractive magnetic field applied during the magnetic particles detecting has an amplitude and duration such that the attractive magnetic field causes only magnetic particles within 35 nm of the binding surface to travel to the binding surface before detecting the magnetic particles.

11. The method according to claim 1, wherein the component of the attractive magnetic field parallel to the binding surface applied during the detecting of the magnetic particles is configured such that the magnetic particles form horizontal multiple-particle clusters.

12. The method according to claim 1, wherein the sequence of repulsive magnetic fields and attractive magnetic fields is repeated at least twice before detecting the magnetic particles.

13. The method according to claim 1, wherein the magnetic particles are detected at the binding surface using a two-dimensional CCD sensor that has a shutter time or frame rate which is synchronized with the start time of the attractive magnetic field applied for detecting the magnetic particles such that one or more images are generated between 0.1 seconds and about 1 second after the start of the attractive magnetic field.

14. The method according to claim 2, wherein the attractive magnetic field applied during the magnetic particles detecting has an amplitude and duration such that only magnetic particles within about 35 nm of the binding surface travel to the binding surface before detecting the magnetic particles.

15. The method according to claim 2, wherein the component of the attractive magnetic field parallel to the binding surface applied during the detecting of the magnetic particles is configured such that the magnetic particles form horizontal multiple-particle clusters.

16. The method according to claim 2, wherein the magnetic particles are detected at the binding surface using a two-dimensional CCD sensor that has a shutter time or frame rate which is synchronized with the start time of the attractive magnetic field applied during the detecting of the magnetic particles such that one or more images are generated between about 0.1 seconds and about 1 second after the start of the attractive magnetic field.

17. A method for the detection of magnetic particles in a sample chamber, the method comprising:
generating a first attractive magnetic field which attracts magnetic particles to a binding surface to promote binding the magnetic particles to the binding surface;
generating a repulsive magnetic field which repels magnetic particles which are not bound to the binding surface away from the binding surface;
applying a second attractive magnetic field which attracts the magnetic particles toward the binding surface;
during the second attractive magnetic field, at a predetermined time after a start of the second attractive magnetic field, detecting magnetic particles at the binding surface,
wherein the predetermined time after the start of the second attractive magnetic field is between about 0.01 seconds and about 1 second.

18. The method according to claim 17, wherein the predetermined time after the start of the second attractive magnetic field is a time during which the magnetic particles travel not more than 35 nm away from the binding surface under the influence of the second attractive magnetic field.

19. A sensor device for the detection of magnetic particles, the sensor device comprising:
a sample chamber with a binding surface;
one or more magnets configured to alternately attract magnetic particles in the sample chamber toward the binding surface and repel the magnetic particles away from the binding surface;
a detector configured to detect magnetic particles at the binding surface; and
one or more processors configured to control the magnets and the detector to perform the method according to claim 2.

* * * * *